United States Patent
Lindigkeit

(10) Patent No.: US 7,041,251 B2
(45) Date of Patent: May 9, 2006

(54) DENTAL CASTING ALLOY

(75) Inventor: Juergen Lindigkeit, Königsbach-Stein (DE)

(73) Assignee: Dentaurum J.P. Winkelstroeter KG, Ispringen (DE)

(*) Notice: Subject to any disclaimer, the term of this patent is extended or adjusted under 35 U.S.C. 154(b) by 291 days.

(21) Appl. No.: 10/460,539

(22) Filed: Jun. 12, 2003

(65) Prior Publication Data

US 2004/0109785 A1 Jun. 10, 2004

(30) Foreign Application Priority Data

Jun. 13, 2002 (DE) ................................ 102 26 221

(51) Int. Cl.
*C22C 19/07* (2006.01)

(52) U.S. Cl. ...................... 420/436; 148/425; 433/207

(58) Field of Classification Search ................ 148/425; 420/436; 433/207
See application file for complete search history.

(56) References Cited

U.S. PATENT DOCUMENTS

| 2,763,547 | A | * | 9/1956 | Dyrkacz et al. ............ 420/440 |
| 3,837,838 | A | | 9/1974 | Mohammed |
| 4,116,724 | A | * | 9/1978 | Hirschfeld et al. ......... 148/674 |
| 4,436,697 | A | | 3/1984 | Friedrich et al. |
| 4,459,263 | A | | 7/1984 | Prasad |
| 4,483,821 | A | | 11/1984 | Prasad |
| 4,491,561 | A | | 1/1985 | Mann |
| 4,606,887 | A | | 8/1986 | Hausselt et al. |
| 4,830,824 | A | | 5/1989 | Lindigkeit |
| 5,039,574 | A | | 8/1991 | Kulmburg |
| 5,227,131 | A | * | 7/1993 | Weigand ..................... 420/436 |
| 5,556,420 | A | | 9/1996 | Mortazavi et al. |
| 5,799,386 | A | | 9/1998 | Ingersoll et al. |
| 6,656,420 | B1 | | 12/2003 | Prasad et al. |
| 6,756,012 | B1 | | 6/2004 | Prasad |
| 2002/0004018 | A1 | | 1/2002 | Prasad et al. |
| 2002/0041820 | A1 | | 4/2002 | Prasad |

FOREIGN PATENT DOCUMENTS

| DE | 36 09 184 C2 | 9/1987 |
| DE | 41 23 606 A1 | 7/1991 |
| DE | 198 15 091 C2 | 4/1998 |
| EP | 0 509 910 A1 | 4/1992 |
| FR | 2 733 416 | 10/1996 |

OTHER PUBLICATIONS

The American Heritage Dictionary of the English Language, 1976, pp. 184 and 243.*

* cited by examiner

*Primary Examiner*—John P. Sheehan
(74) *Attorney, Agent, or Firm*—Leydig, Voit & Mayer, Ltd.

(57) ABSTRACT

To improve the fracture resistance of a dental casting alloy without giving rise to undue hardness thereof it is proposed that the dental casting alloy substantially consists of

| 28–34 | wt % | Cr, |
| 5–9 | wt % | Mo, |
| 1–3 | wt % | W, |
| 0.9–1.3 | wt % | Si, |
| 0.15–0.3 | wt % | Mn, |
| 0.1–0.3 | wt % | N, |
| 0.1–0.3 | wt % | C, |
| <0.1 | wt % | Ni, | manufacturing impurities,
remainder cobalt,
the ratio of the content of Mo to that of W being in the range of from about 3:1 to about 5:1 and the ratio of the content of Si to that of Mn being in the range of from about 3:1 to about 9:1.

2 Claims, No Drawings

DENTAL CASTING ALLOY

This invention pertains to a dental casting alloy for fabricating dental prosthesis frameworks.

Casting alloys for dental prosthesis frameworks, particularly for so-called model cast prostheses, have been known since 1935.

Such model casting alloys contain, in addition to chromium and molybdenum, high proportions of carbon, in order to achieve an appropriate degree of dentally necessary rigidity and an easily liquefiable melt, which facilitates precise decantation from the models.

The addition of manganese and silicon is to these alloys is necessary in order to have a positive influence on their flowability.

DE 36 09 184 C2 discloses the use of an alloy for fabricating dental castings in dentistry. This alloy has relatively low molybdenum contents and a ratio of the silicon to manganese contents of less than 1.

DE 198 15 091 C2 discloses an alloy for dental castings, which provides for silicon and manganese contents of up to 3 wt % and, in addition, prescribes a content of from 0.05 to 1.2 wt % of tantalum, niobium, and/or tungsten, whilst the portion of each individual element tantalum, niobium, or tungsten is less than 0.5 wt %. The range in which nitrogen may be present is from 0.05 to 0.4 wt %.

The use of nitrogen for raising the strain at break without loss of stability is known per se in metallurgy. This type of compensation is, however, detrimental to the laser-welding property of the alloy, as explained in detail in DE 198 15 091 C2.

Alloys to be used in dentistry must satisfy special general requirements. For example, burning-on alloys for powder metallurgy must be compatible with commercial dental ceramics as regards thermal expansion and contraction. In addition, these alloys must be capable of forming a thin oxide layer guaranteeing adhesion between metallic and ceramic surfaces. In addition, the color of the oxide may not show through the opaque porcelain for esthetic reasons. In the case of dental castings that are not to be veneered, eg, removable prostheses with clips, a certain activation capacity and resilient hardness are required. Another particularly important factor in dentistry is that processing of the alloys used should be possible in the dental laboratory using available means, ie they should be capable of being cast with conventional centrifugal casters. For this reason alloys frequently used in dental alloying have, when used as casting material, a much higher carbon content than is permitted by various standards. Furthermore, those dental casting alloys are to be preferred whose hardness in the cast state does not deviate to an extensive degree from the hardness of natural dental enamel so that no appreciable abrasive wear of the tooth is caused by contact of the dental casting alloy with the surface of the tooth. Furthermore, it is advantageous when the alloy can be produced with a low nickel content so that patients who are allergic to nickel can also be provided with such prostheses.

It is an object of the present invention to provide, within the aforementioned restrictions, a casting alloy of the above type which exhibits a high flexural strength value but still does not show an excessively high Vickers hardness (HV 10).

It is another object of the invention to provide a casting alloy particularly suitable for dental prosthetic constructions which exhibit excellent flexural strength without having unduly enhanced hardness (Vickers hardness HV 10).

These objects are achieved according to the invention in the dental casting alloy defined above in that said alloy substantially comprises

| | | |
|---|---|---|
| 28–34 | wt % | chromium |
| 5–9 | wt % | molybdenum |
| 1–3 | wt % | tungsten |
| 0.9–1.3 | wt % | silicon |
| 0.15–0.3 | wt % | manganese |
| 0.1–0.3 | wt % | nitrogen |
| 0.1–0.3 | wt % | carbon | and a nickel content of less than 0.1 wt %.

Also present are manufacturing impurities of less than 0.1 wt % in each case, the remainder being cobalt.

It should be noted that, within the scope of the invention, the ratio of the content of Mo to that of W is in the range of from about 3:1 to about 5:1 and the ratio of the content of Si to that of Mn is in the range of from about 3:1 to about 9:1. It has been found, surprisingly, that when a certain ratio of silicon to manganese and at the same time relatively low contents of carbon and nitrogen are maintained, as stated above, no great increase in the hardness is attained with the aforementioned tungsten contents even in the case of high contents of molybdenum and chromium, whilst at the same time the flexural strength retains a surprisingly high value despite the high content of chromium and molybdenum and despite the additional content of tungsten and, in addition, good laser weldability of the alloy is achieved on account of the low contents of nitrogen.

Preferably the content of tungsten in the alloy is from 1 to 2 wt %.

Below there is given a concrete example of a composition of the alloy of the invention (Table 1), while it may be emphasized that the invention is not, of course, limited to this particular alloy. The following Table 2 lists the mechanical properties of the alloy as shown in Table 1.

TABLE 1

| Elementary Composition | Percentage by weight |
|---|---|
| Co | 58.4 |
| Cr | 32 |
| Mo | 6.5 |
| W | 1.5 |
| Mn | 0.2 |
| Si | 1 |
| N | 0.2 |
| C | 0.2 |

TABLE 2

| Mechanical Properties | |
|---|---|
| Apparent Yield Point $R_p$ 0.2 (MPa) | 710 |
| Tensile Strength $R_m$ (MPa) | 949 |
| Elongation at Break $A_5$ (%) | 6.6 |
| Vickers Hardness HV 10 | 369 |

What is claimed is:

1. A dental casting alloy, particularly for fabricating dental prosthesis frameworks, substantially comprising

| | | |
|---|---|---|
| 28–34 | wt % | Cr, |
| 5–9 | wt % | Mo, |
| 1–3 | wt % | W, |
| 0.9–1.3 | wt % | Si, |
| 0.15–0.3 | wt % | Mn, |
| 0.1–0.3 | wt % | N, |
| 0.1–0.3 | wt % | C, |
| <0.1 | wt % | Ni, | manufacturing impurities, remainder cobalt, the ratio of the content of Mo to that of W being in the range of from about 3:1 to about 5:1 and the ratio of the content of Si to that of Mn being in the range of from about 3:1 to about 9:1.

2. An alloy as defined in claim 1, characterized in that the content of tungsten ranges from about 1 to about 2 wt %.

* * * * *